United States Patent [19]
Haga

[11] Patent Number: 5,715,050
[45] Date of Patent: Feb. 3, 1998

[54] OPTICAL INSPECTION APPARATUS INCLUDING A TELECENTRIC OPTICAL SYSTEM, AN APERTURE STOP AND A SCREEN

[75] Inventor: Kazumi Haga, Chofu, Japan

[73] Assignee: New Creation Co., Ltd., Tokyo-to, Japan

[21] Appl. No.: 590,637

[22] Filed: Jan. 24, 1996

[51] Int. Cl.[6] .................... G01N 21/00; G02B 21/00
[52] U.S. Cl. .............. 356/237; 359/363; 359/369; 250/559.17; 250/559.44
[58] Field of Search ................ 356/237; 359/363, 359/369, 389, 388; 250/559.08, 559.17, 559.44

[56] References Cited

U.S. PATENT DOCUMENTS

| | | | |
|---|---|---|---|
| 4,256,363 | 3/1981 | Briones | 359/369 |
| 4,469,442 | 9/1984 | Reich | 356/237 |
| 4,963,724 | 10/1990 | Neumann | 359/369 |
| 5,289,260 | 2/1994 | Miyazaki et al. | 356/237 |
| 5,519,496 | 5/1996 | Borgert et al. | 356/237 |

FOREIGN PATENT DOCUMENTS

WO 90/05319  5/1990  European Pat. Off. ........ 359/369

*Primary Examiner*—Jon W. Henry
*Attorney, Agent, or Firm*—Evenson, McKeown, Edwards & Lenahan, P.L.L.C.

[57] ABSTRACT

There is provided an optical inspection apparatus including an illuminating block for emitting light and illuminating a sample with the emitted light, an observing optical system for forming an image from transmitted light or reflected light from the sample, and an observing block for observing the image. The observing optical system comprises an object side lens arranged on an object side close to the sample, an image side lens arranged on an image side remote from the sample, the object side lens and the image side lens being arranged such that the object side lens and the image side lens have focal points coincident to each other, forming a both-side telecentric optical system for acting on the transmitted light or the reflected light to form the image, an aperture arranged on the focal points or in the vicinity thereof, and a screen arranged on a back focal point of the image side lens or in the vicinity thereof for having the image of the sample being projected thereon. The observing block is arranged such that the image of the sample projected on the screen is observed from a rear side of the screen remote from the sample.

11 Claims, 4 Drawing Sheets

OPTICAL INSPECTION APPARATUS INCLUDING A TELECENTRIC OPTICAL SYSTEM, AN APERTURE STOP AND A SCREEN

BACKGROUND OF THE INVENTION

1. Field of the Invention

This invention relates to an optical inspection apparatus for two-dimensionally observing the surface of a sample, etc., and more particularly to an optical inspection apparatus of this kind for checking conditions of the surface of a sample, such as a mirror-finished surface wafer, or detecting an identifier, especially, an identification (ID) number, formed by projections and/or recesses in the sample surface.

2. Prior Art

The present assignee has already proposed an optical inspection apparatus which employs a telecentric optical system for detecting an ID number formed in the surface of a semiconductor wafer as a component part for semiconductor integrated circuits, or checking conditions of the surface of a sample, such as an undulation, a dimple, a projection, insufficient wash, and buff damage (Japanese Patent Application No. 6-162848). This optical inspection apparatus includes an illuminating optical system for illuminating a sample, such as a semiconductor wafer, with parallel light converted from halogen light, an observing optical system for forming an image from light reflected from the sample, and an observing block for observing the image formed by the observing optical system. The observing optical system has a lens (optical element) for converging the light reflected from the sample, an aperture stop arranged at a back focal point of the lens, and a telecentric optical system arranged on a side of the aperture remote from the sample for converting the light having passed through the aperture to parallel light.

In this optical inspection apparatus, when the parallel light is irradiated onto the sample, the reflected light therefrom is converged by the lens, and passes through the aperture stop to enter the telecentric optical system. The telecentric optical system converts the incident light into parallel light, and forms an image on the air at a predetermined location according to the focal length thereof. The observer observes the image of the sample by focusing observing means on the image on the air.

However, since the optical inspection apparatus employs the observing means for observing the image on the air, the image of the sample is low in contrast, which can cause e.g. an erroneous recognition of the ID number and even incapability of recognition of the same. That is, the image on the air contains components ascribable to small irregularities of the sample surface which are irrelevant to observation or recognition of the ID number, and components unnecessarily having passed through the aperture stop. Therefore, in recognizing the ID number based on a picture signal picked up by the observing means, if a predetermined level of light is used as a threshold value, and recognizing process is carried out such that an image formed by light which is higher or lower in level than the threshold value should correspond to the ID number, an image which does not correspond to the actual ID number can be produced due to noise and unnecessary components whose level fluctuates across the threshold value, resulting in an erroneous recognition of the ID number.

Further, in the proposed optical inspection apparatus, the image on the air, which is formed in the air, is observed by the observing means, and accordingly, the telecentric optical system is provided within the observing means of which the entrance pupil is positioned at infinity. This makes the construction of the observing means rather complicated.

Further, depending on the direction from which the sample is observed, it becomes easy or difficult to observe the sample due to unnecessary reflected components. To overcome such inconvenience, in the proposed optical inspection apparatus, the sample is slightly tilted as required to observe an image thereof with ease. A tilt stage is thus required to be provided for tilting the sample through a very small angle. The tilt stage, however, is expensive and causes an increase in the manufacturing cost. On the other hand, it can be contemplated to cause halogen light to enter a plurality of optical fibers and emit therefrom at angles set such that they are slightly different from each other, and then, select one of the optical fibers so as to set the incidence of light on the sample at the optimum angle. In this event as well, the manufacturing cost is increased since the optical fibers are expensive, and moreover, not only apertures have to be provided on the outgoing side of the optical fibers, but also shutters for closing the apertures and even aperture-driving devices are required to be provided.

Further, in the case of the halogen light source, it takes much time before the intensity of the halogen light becomes stable, so that the illuminating optical system using the halogen light source suffers from the problem that a long preparation time period is required before starting the inspection.

SUMMARY OF THE INVENTION

It is an object of the invention to provide an optical inspection apparatus which is capable of improving the contrast of an image of a sample to be observed, as well as simplifying observing means and reducing the manufacturing cost.

To attain the object, the invention provides an optical inspection apparatus including an illuminating block for emitting light and illuminating a sample with the emitted light, an observing optical system for forming an image from transmitted light or reflected light from the sample, and an observing block for observing the image.

The optical inspection apparatus according to the invention is characterized in that the observing optical system comprises:

an object side lens arranged on an object side close to the sample;

an image side lens arranged on an image side remote from the sample;

the object side lens and the image side lens being arranged such that the object side lens and the image side lens have focal points coincident to each other, forming a both-side telecentric optical system for acting on the transmitted light or the reflected light to form the image, an aperture stop arranged on the focal points or in the vicinity thereof; and a screen arranged on a back focal point of the image side lens or in the vicinity thereof for having the image of the sample being projected thereon;

and that the observing block is arranged such that the image of the sample projected on the screen is observed from a back side of the screen remote from the sample.

According to the optical inspection apparatus of the present invention, when the sample is illuminated with light from the illuminating block, the transmitted light or reflected light from the sample is converged by the object side lens and then passes through the opening of the aperture stop to enter the image side lens. Then, the light emitted from the image side lens illuminates the screen to project an image of the sample thereon. By observing the projected image by means of the observing block, it is possible to observe the surface of the sample or the interior of the sample, as an image having a pattern of light and dark portions. The screen diffuses light received from the image side lens to smooth it. This narrows the overall range of brightness level, but sufficiently smoothes noise components. As a result, it becomes easy to effect digital processing of a picture signal, to thereby enhance the contrast of the image. When an ID number is to be recognized after the digital processing, for example, an erroneous recognition of the ID number due to noise can be avoided, thereby positively enhancing the correct recognition rate.

Now, the principle of the invention will be described with reference to FIG. 5. The light emitted from the both-side telecentric optical system has noise components as small irregularities of intensity of light ascribable to small irregularities of the surface of the sample, etc. as indicated by broken lines in the figure. The noise components are superposed on light which forms an image of the sample to be observed. Therefore, in recognizing the ID number based on a picture signal picked up by the observing means, the level of light fluctuates across a threshold value with reference to which an image of the ID number is formed as part having a higher or lower level of light than the threshold value. This produces an image which does not correspond in shape to an actual shape of the ID number, causing an erroneous recognition of the ID number. However, by projecting the light on the screen, the overall range of brightness level is reduced, but the noise components are smoothed, whereby the noise components fluctuating across the threshold level are eliminated. As a result, the ID number can be reliably recognized.

Further, since the image is projected on the screen, a camera lens of an ordinary type can be employed for the observing means, and the image can be easily observed by focusing the camera lens onto the image. This contributes to a simplified lens arrangement of the observing block, and consequently reduction of the manufacturing cost of the optical inspection apparatus.

Preferably, the illuminating block includes a half mirror arranged between the object side lens and the image side lens for reflecting the emitted light toward the sample, a plurality of light sources for emitting light toward the half mirror at respective angles of emission different from each other, and a lighting control block for selectively lighting one of the plurality of light sources.

According to this preferred embodiment, the plurality of light sources can be selectively and sequentially lighted. The light sources emit light toward the sample at respective angles of emission different from each other. Therefore, in viewing an ID number in the form of grooves formed in the surface of a sample, for example, either a bright-field or a dark-field which is easy to view can be selected for observation depending on the angle of slope of the grooves formed on the sample surface.

More preferably, the light sources are each formed by an LED constructed to emit a divergent pencil of rays.

According to this preferred embodiment, since the light sources are formed by LED's constructed such that each emit a divergent pencil of rays, compared with a case of an optical inspection apparatus using a laser beam as a source of light, it is possible to reduce the manufacturing cost, and further, the emitted light from the LED becomes stable immediately after the power is turned on, which makes it unnecessary to secure a preparation time period before the light source is stabilized.

Preferably, at least one of the object side lens and the image side lens is an aspheric lens.

According to this preferred embodiment, since at least one of the object side lens and the image side lens is an aspheric lens, the focal lengths of the lenses of the both-side telecentric optical system can be reduced, which makes it possible to design the optical inspection apparatus compact.

Preferably, the optical inspection apparatus includes means for rotating the screen when the sample is observed.

According to this preferred embodiment, rotation of the screen evens the irregularities on the surface of the screen, which prevents the light transmitted therethrough from having components of different levels ascribable to the irregularities on the surface of the screen.

The above and other objects, features, and advantages of the invention will become more apparent from the following detailed description taken in conjunction with the accompanying drawings.

DETAILED DESCRIPTION

The invention will now be described in detail with reference to drawings showing an embodiment thereof.

Figure 1:
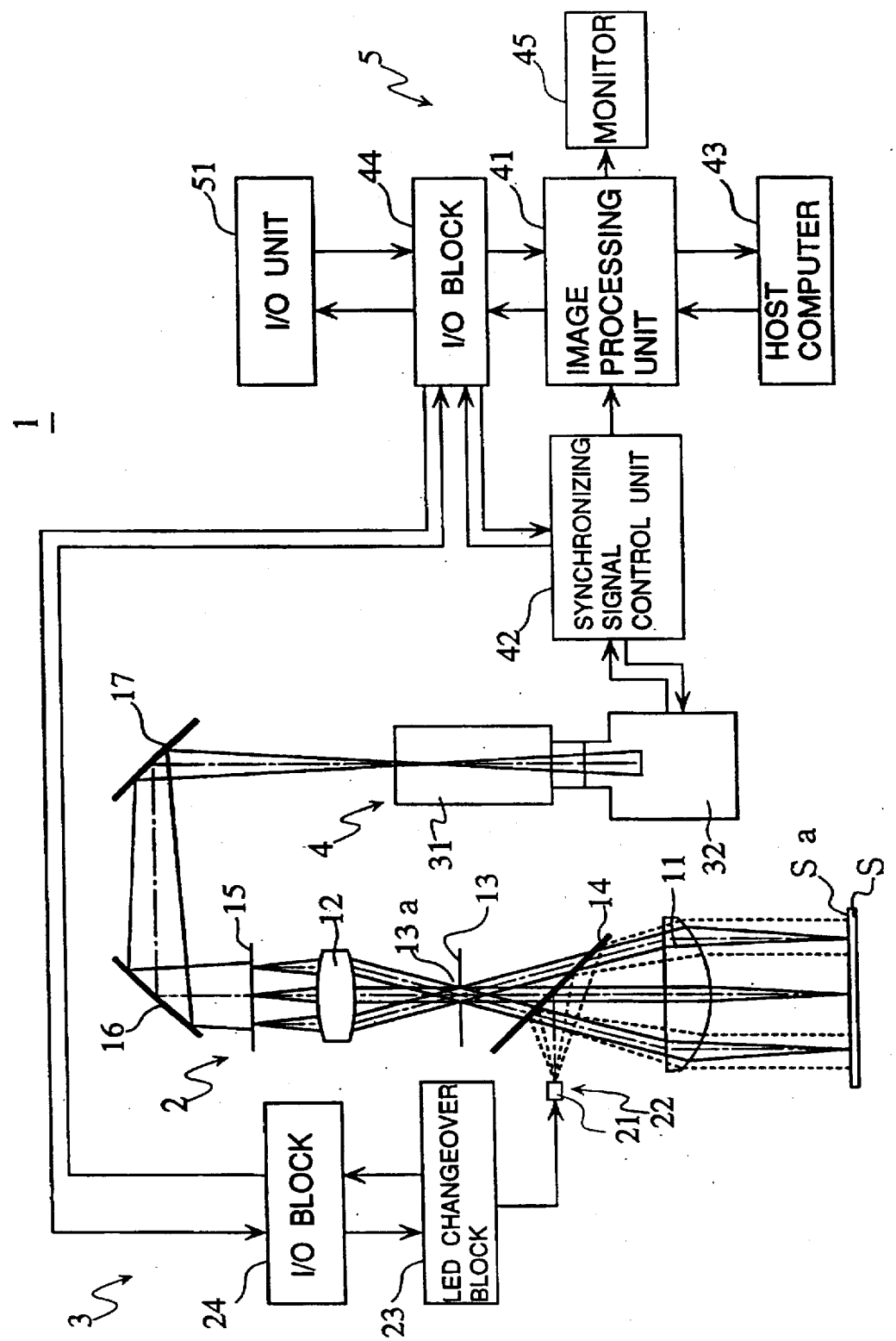
FIG. 1 is a block diagram showing the arrangement of an optical inspection apparatus according to an embodiment of the invention.

Referring first to FIG. 1, there is shown an optical inspection apparatus 1, an observing optical system 2, an illuminating block 3, an observing block 4, and a control block (lighting control block) 5.

The optical inspection apparatus 1 observes ID numbers, irregularities, etc. (hereinafter referred to as "observed portion") formed on the surface Sa of a sample S (hereinafter referred to as "the sample surface"), such as a semiconductor wafer, placed on a stage, not shown, by means of a CCD camera 32. More specifically, the sample S is illuminated with the light emitted from the illuminating block 3, and the light reflected from the surface Sa of the sample S forms an image of the sample surface Sa within the observing optical system 2. The formed sample image is picked up by the CCD camera 32 within the observing block 4.

The observing optical system 2 is comprised of an object side lens 11 arranged on a sample side close to the sample and an image side lens 12 arranged on a side remote from the sample, where the image of the sample is picked up. These lenses 11, 12 are arranged such that the back focal point of the object side lens 11 and the front focal point of the image side lens 12 are substantially coincident to each other. The lenses 11, 12 cooperate to form a so-called both-side telecentric optical system. The observing optical system 2 is comprised of an aperture stop 13 arranged on the back focal point of the object side lens 11 and having an opening 13a, a half mirror 14 arranged between the object side lens 11 and the aperture stop 13, a screen 15 arranged on the back focal point of the image side lens 12, and total reflection mirrors 16, 17 arranged on the back side of the screen 15.

The lenses 11, 12 are aspheric lenses, and the lens surface of the object side lens 11 facing toward the sample S and the lens surface of the image side tens 12 facing toward the screen 15 are formed aspheric, and the lens surfaces of the lenses 11, 12 on the other or remaining sides are formed spherical. As a result, the focal lengths of the lenses 11, 12 are reduced, and hence the observing optical system 2 can be made compact. Further, both the lenses 11, 12 are each formed of a single lens, which contributes to reduction of the manufacturing cost. Further, the observing optical system 2 is constructed such that the spherical aberration thereof is very small, which enables the CCD camera 32 to pick up the image of the sample S with a high fidelity. Further, the object side lens 11 converts a divergent pencil of rays emitted from an LED 21, described in detail hereinafter, and then reflected from the half mirror 14 into parallel light to emit the same toward the sample S. Further, the image side lens 12 converges the light having passed through the opening 13a of the aperture stop 13 into parallel light, to emit the same onto the screen 15.

Details of specifications of the lenses 11, 12 and the aperture stop 13 are shown in TABLE 1 below. Symbol numbers 1 to 5 in the table correspond to the lens surface of the object side lens 11 facing toward the sample S, the lens surface of the object side lens 11 facing toward the half mirror 14, the aperture stop 13, the lens surface of the image side lens 12 facing toward the aperture stop 13, and the lens surface of the image side lens 12 facing toward the screen 15, respectively.

TABLE 1

| SYMBOL NUMBER | RADIUS OF CURVATURE (mm) | DISTANCE BETWEEN SURFACES (mm) | INDEX OF REFRACTION | EFFECTIVE RADIUS (mm) |
| --- | --- | --- | --- | --- |
| 1 | 30.1 | 15.0 | 1.51 | 25.0 |
| 2 | ∞ | 48.5 | 1.00 | 25.00 |
| 3 | / | 27.0 | 1.00 | / |
| 4 | 45.9 | 10.0 | 1.51 | 15.0 |
| 5 | −20.7 | 0.0 | 1.00 | 15.0 |

Further, the aspheric coefficients, fourth-order coefficients, and sixth-order coefficients of the lenses 11, 12 are shown in TABLE 2 below. In this case, symbols numbers 1 and 5 correspond to those of TABLE 1. The aspheric coefficients and the like are coefficients used in Equation (1). In Equation (1), "Z" represents coordinates of a lens surface, "C" a radius of curvature, "K" an aspheric coefficient, "$h^2$" height of an object, "A" a fourth-order coefficient, "B" a sixth-order coefficient, "C" an eighth-order coefficient, and "D" a tenth-order coefficient. In the present embodiment, the sixth-order to tenth-order coefficients of the object side lens 11 are equal to "0", and the eight-order and tenth-order coefficients of the image side lens 12 are equal to "0".

TABLE 2

| SYMBOL NUMBER | ASPHERIC COEFFICIENT | 4-TH ORDER COEFFICIENT | 6-TH ORDER COEFFICIENT |
| --- | --- | --- | --- |
| 1 | −0.61 | 2.4E-07 | / |
| 5 | −7.1 | −3.4E-05 | 9.4E-08 |

$$Z = Ch^2/[1 + \{1 - (K + 1)C^2h^2\}^{1/2}] + Ah^4 + Bh^6 + Ch^8 + Dh^{10} \ldots (1)$$

Figure 2:
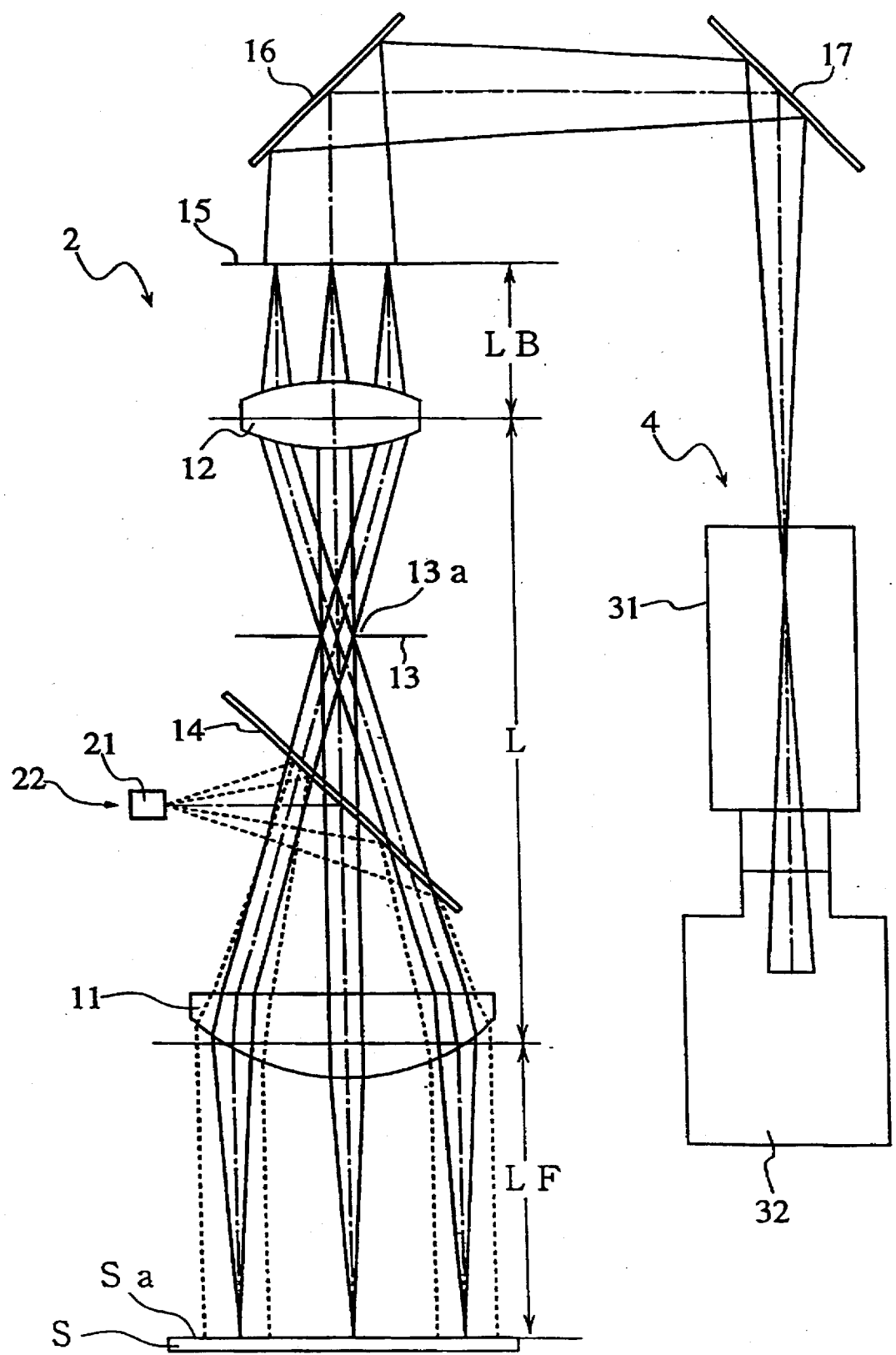
FIG. 2 is a block diagram showing the arrangement of an observing optical system appearing in FIG. 1.

Further, the lenses 11 and 12 are arranged such that "LF", "L" and "LB" appearing in FIG. 2 are equal to approximately 58 mm, approximately 100.5 mm, and approximately 26.9 mm, respectively.

The aperture stop 13 is formed by an iris diaphragm having ten blades, and it is possible to continuously vary the diameter of its circular opening 13a by actuating a movable adjustment part, not shown. Through continuous variation of the diameter of the opening 13a, it is possible to adjust the contrast of the image of the sample picked up a camera lens 31, referred to hereinafter.

The half mirror 14 is inclined with respect to the optical axis of the object side lens 11 for reflecting the light emitted from the illuminating block 3 toward the sample S to illuminate the same, and for permitting the light reflected from the sample surface Sa and then converged by the object side lens 11 to pass therethrough toward the image side lens.

The light converged by the image side lens 12 illuminates the screen 15 whereby the image of the sample surface Sa is made real or caused to appear thereon. To this end, the screen 15 is formed of a semi-transparent material which is capable of visualizing a light pattern of bright and dark portions thereon, such as a finely-felted paper, a tracing paper, and a frosted glass. The screen 15 slightly disperses or diffuses light components reflected from the observed portion and having a greater intensity, and light components reflected e.g. from a background of the observed portion and having a slightly weaker intensity, to smooth the both kinds of light components, thereby eliminating noise components of light. This reduces the overall intensity level of light, but the noise components, such as the light components ascribable to very small irregularities of the sample surface Sa and components having unnecessarily passed through the aperture 13 are smoothed, which makes it easy to perform digital processing of data of the picked-up image, thereby improving the contrast of the observed portion against the background thereof. As a result, when the ID number is recognized after image data is subjected to digital processing, it is possible to prevent an erroneous recognition of the number, which could otherwise occur due to noise, and reliably improve the correct recognition rate.

Figure 3A:
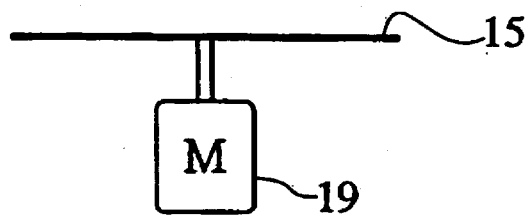
FIG. 3A is a side elevation showing a screen appearing in FIG. 1.
Figure 3B:
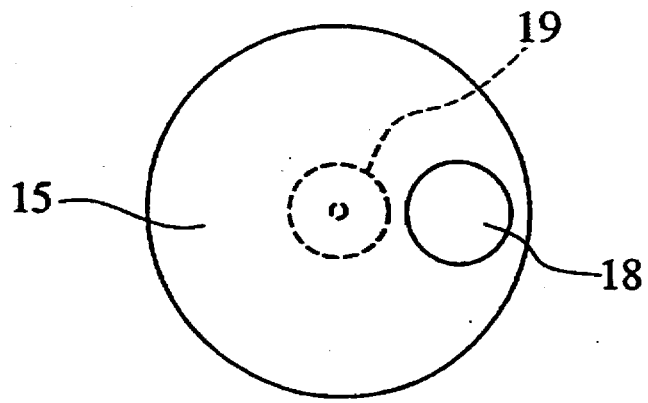
FIG. 3B is a plan view showing the screen.
Figure 4A:
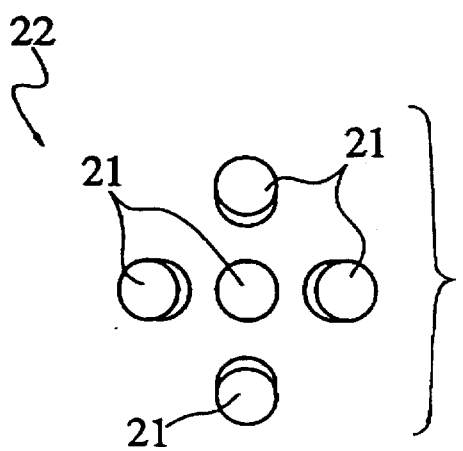
FIG. 4A is a front elevation showing an LED block appearing in FIG. 2.
Figure 4B:
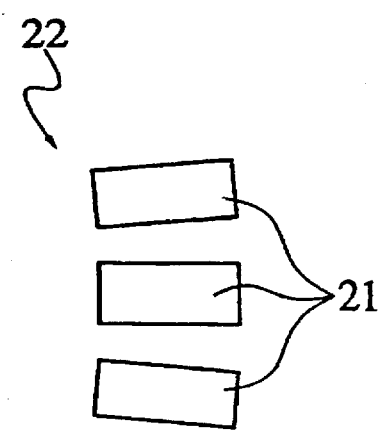
FIG. 4B is a side elevation showing the LED block.
Figure 5:
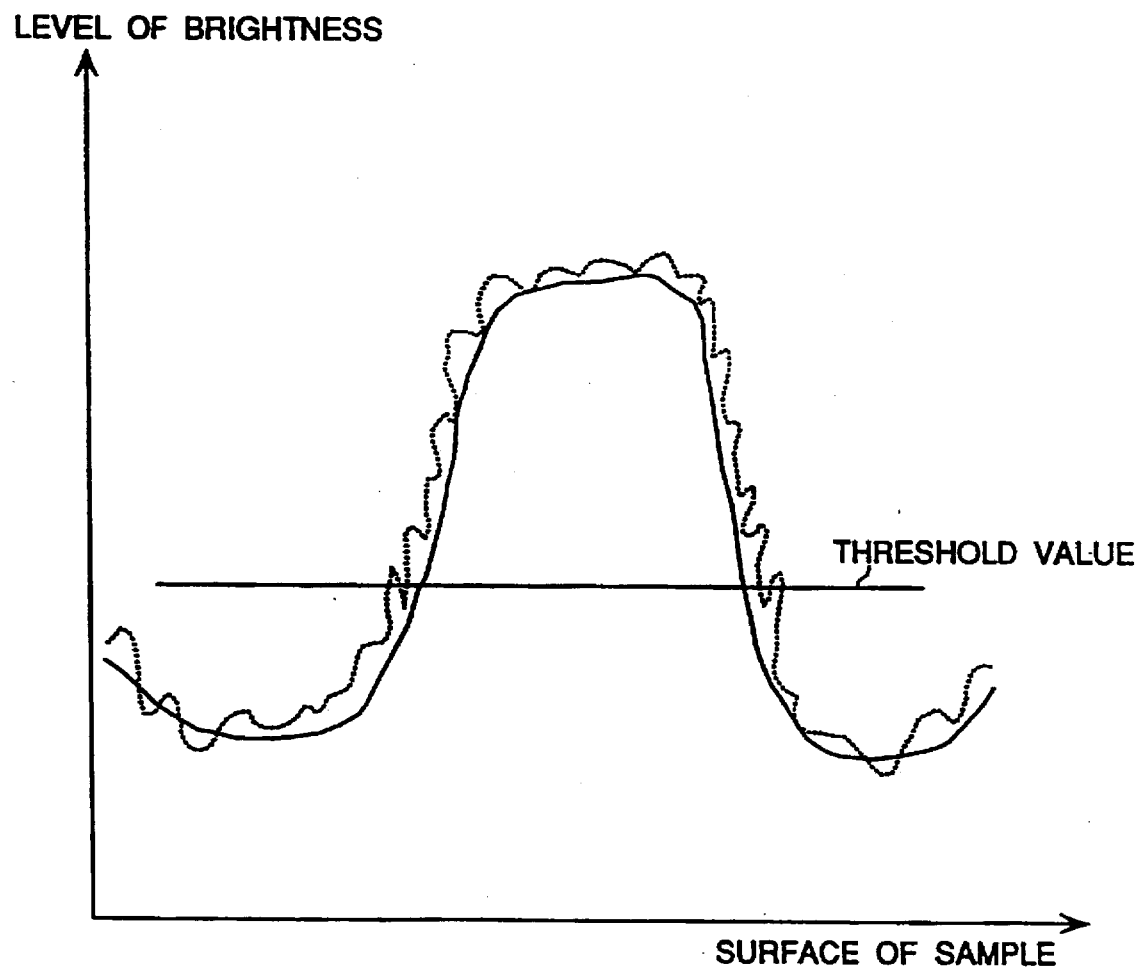
FIG. 5 is a diagram which is useful in explaining the principle of the present invention for improving the contrast by the use of the screen.

When a paper having small irregularities on the surface thereof is used as the screen 15, different levels of light are permitted to pass therethrough, which produces an erroneous image of the sample. Therefore, in such a case, it is preferred that the screen 15 is rotated to even or average the irregularities of the surface of the screen surface. To this end, according to the present embodiment, as shown in FIGS. 3A and 3B, there is used a disc of paper having a radius fairly larger than the maximum diameter of a sample image 18 projected thereon by the light emitted from the image side lens 12, with the paper being fitted on a shaft connected to a motor 19 such that the shaft extends through the center of the paper. By driving the motor for rotation, the paper is rotated to even or average the irregularities on the surface of the paper.

The total reflection mirrors 16, 17 reflect the light having passed through the screen 15 into the observing block 4. In this case, the light having passed through the screen 15 is bent by 90 degrees each of both the total reflection mirrors 16, 17, and then enters the observing block 4. As a result, the observing optical system 2 is reduced in length in a vertical direction and a transverse direction, as viewed from FIG. 1, which contributes to reducing the size of the apparatus 1.

The illuminating block 3 is comprised of the LED block 22 formed of a plurality of LED's (light sources) 21, 21, . . ., which each are capable of generating light having a high brightness, an LED changeover block 23 for controlling the lighting and extinguishing of the LED's 21, 21, . . . , and an I/O block 24 for receiving an LED changeover signal supplied from the control block 5.

The LED block 22 has five LED's 21, 21, ..., which are slightly made different from each other in respect of the angle of emission of light toward the half mirror 14. By selectively lighting one of the LED's 21, 21, ..., it is possible to slightly change the angle of outgoing or emitted light for illuminating the sample S. This makes it possible to select an image which is easy to observe or recognize, when the observed portion is a character written by grooves formed in the sample surface Sa with a slit being provided at the bottom thereof, or a character formed of dots. That is, depending on the direction of observation of the sample, light can be reflected from the bottoms of the grooves and the dots in all directions, and undesirable reflection components are presented, which makes it easy or difficult to view the image of the sample S. However, depending on the angle of inclination of walls of the grooves and the like, one of the LED's 21, 21, ..., can be sequentially lighted to thereby selectively use one of images on either bright-field or dark-field for observation.

The LED selector 23 has switches corresponding to the LED's 21, 21, ..., respectively. The ON/OFF operation of each switch is controlled by the LED changeover signal supplied from the I/O block 24, and a lighting signal is supplied to a selected one of the LED's corresponding to one of the switches turned on, thereby lighting the selected LED 21.

The observing block 4 described above is equipped with the camera lens 31 and the CCD camera 32. The camera lens 31 is constructed such that its magnification can be set as desired, and the range of an observed field can be changed by remote control from the control block 5. The CCD camera 32 picks up a two-dimensional pattern of bright and dark portions of light corresponding to conditions of the sample surface Sa. The picture signal picked up by the CCD camera 32 is supplied via a coaxial cable, not shown, to a synchronizing signal control unit 42 of the control block 5.

The control block 5 includes an image processing unit 41, the synchronizing signal control unit 42, a host computer 43, an I/O block 44, and a monitor 45.

The image processing unit 41 receives the picture signal from the CCD cameras 32 and delivers a video signal to the monitor 45, and at the same time delivers results of recognition after the image processing (e.g. data of recognized characters) to the host computer 43, and via the I/O block 44 to the I/O unit 51. The I/O unit 51 is connected to various controllers, not shown, for a robot or a transfer system, not shown. These controllers control the robot based on a digital picture signal received from the I/O unit 51.

The synchronizing signal control unit 42 incorporates a clock signal generator for generating a plurality of clock signals having different repetition periods. The synchronizing signal control unit 42 delivers a clock signal having a predetermined repetition period to the CCD camera 32, thereby controlling the shutter speed of the CCD camera 32 and the charge-storing time period of the CCD camera 32 in a manner linked to the shutter speed. This makes it possible to control the brightness level of the picture signal. That is, when the light reflected from the sample surface Sa is low in brightness, a clock signal having a long repetition time period is delivered to reduce the shutter speed and at the same time prolong the charge-storing time period, whereas when the same is high in brightness, a clock signal having a short repetition time period is delivered to increase the shutter speed and at the same time shorten the charge-storing time period, thereby making it possible to control the brightness level of the picture signal to a suitable level.

Further, the synchronizing signal control unit 42 delivers a clock signal having a predetermined repetition period via the I/O blocks 44, 24 to the LED changeover block 23, to sequentially turn on internal switches of the LED changeover block 23, whereby the five LED's 21, 21, ... of the LED block 22 are lighted one after another over each repetition time period of the clock signal. At the same time, the synchronizing signal control unit 42 delivers the clock signal via the I/O block 44 to the image processing unit 41. In synchronism with the clock signal supplied from the synchronizing signal control unit 42, the image processing unit 41 delivers the picture signal from the CCD camera 32, i.e. the video signal based on the picture signal corresponding to an image of the sample obtained when the sample is illuminated by each of the five LED's 21, to the monitor 45.

The host computer 43 recognizes the ID number formed on the sample surface Sa from the digital picture signal delivered from the image processing unit 41, checks the production process of semiconductor wafers, and performs various statistical operations, etc. In doing this, the host computer 43 determines based on the five images (i.e. digital picture signals) delivered from the image processing unit 41, e.g. that an ID number is correct, if four or more, or three or more images show the same ID number. Further, after recognizing the ID number, the host computer controls or drives the transfer system and a transfer robot, neither of which is shown, for transferring the following sample onto the stage.

Next, the operation of the optical inspection apparatus will be described with reference to FIGS. 1 and 2.

When the LED changeover signal is delivered from the synchronizing signal control unit 42, the LED's 21, 21, ... are sequentially lighted to each emit a pencil of rays toward the half mirror 14 from directions slightly different from each other. Each pencil of rays is reflected from the half mirror 14 to sequentially illuminate the sample surface Sa from directions slightly different from each other. Each pencil is reflected from the sample surface Sa in a substantially normal direction, and travels in a direction opposite to that of the illuminating or outgoing light, thereby transmitting through the half mirror 14, passing through the opening 13a of the aperture stop 13 to enter the image side lens 12. Irregularly reflected light from the sample surface Sa is intercepted by the aperture stop 13, which enhances the contrast of the image obtained by the picture signal. The light incident on the image side lens 12 is converted to parallel light. The parallel light emitted from the image side lens 12 illuminates the screen 15 to thereby project the image of the sample surface Sa on the screen 15.

Then, by focusing the CCD camera 32 on the screen 15, the image of the sample surface Sa is picked up by the CCD camera 32. A pattern of light and dark portions of the sample image projected on the screen 15 reflect the ID number, irregularities formed on the sample surface Sa, or the like, which makes it possible to observe a two-dimensional distribution of subtle changes on the conditions of the sample surface Sa by observing the picture output. In this case, the screen 15 improves the contrast of the observed portion and the background thereof.

Further, in viewing the observed portion, the most suitable one of the five images respectively corresponding to the five LED's 21, 21, ..., can be selected for observation, which makes it possible to view the observed portion in a reliable manner with ease. More specifically, in the present embodiment, the sample surface Sa is illuminated sequentially by the five LED's from the respective directions different from each other. As a result, five's kinds of images of the sample surface Sa are picked up, and one of them is selected by selecting means, not shown. This makes it possible to select one of the picked-up images most suitable for observation with ease, without adjusting the inclination of the stage.

As described heretofore, according to the present embodiment of the invention, the screen arranged on the back focal point of the image side lens 12 improves the contrast of the sample image. Further, the CCD camera 32 can pick up a real image projected on the screen, which dispenses with a complicated lens system, such as a telecentric optical system, for the camera lens 31, but a camera lens of an ordinary type can be suitably employed instead. This simplifies the construction of the camera lens 31, which results in a reduced manufacturing cost of the optical inspection apparatus.

Further, a sample image suitable for observation can be easily obtained or selected by sequentially lighting a plurality of LED's 21, 21, ..., which are slightly different in angles of emission of light toward the half mirror 14. Further, the intensity of light generated by the LED's 21 becomes stable immediately after the power is turned on, which makes it possible to reduce a observing time period, and reduce the manufacturing cost of illuminating block 3 compared with a case in which a laser beam source, a halogen lamp, or the like is employed.

While the invention has been described in its preferred embodiment, it is to be understood that the invention is not limited thereto, and that various changes and modifications may be made without departing from the sprit and scope thereof.

For example, although the lenses 11, 12 each have a single aspheric surface, this is not limitative, but both surfaces of each lens may be made aspheric, or the surface of the object side lens 11 on the aperture 13 side and the surface of the image side lens 12 on the aperture 13 side may be made aspheric.

Further, the number of LED's 21 is not limited to five, but may be more or less than five. Further, as the light source used in the illuminating block 3, a halogen lamp or an xenon lamp may be used.

Further, although in the above embodiment, the CCD camera 32 is used to observe the image, this is not limitative, but the observing block 4 may be constructed such that the image can be observed with a camera of an ordinary type, any suitable kind of image pick up device including a photoelectric tube, such as a photomultiplier, or the naked eye.

Further, in the image processing unit 41, an original picture signal contained in the signal received from the CCD camera 32 may be differentiated to obtain a differential signal, and then the differential signal may be added to the original picture signal to amplify a low contrast in the original picture signal for display. Further, there may be provided a brightness adjusting circuit for adjusting the brightness level of the picture signal resulting from the addition, as desired. The brightness adjustment enables a picture or image to be observed with the optimum brightness e.g. when the condition of the inside of a contour formed by recessed or projected part of the observed portion or the contour itself is to be observed.

Further, although in the above embodiment, an iris diaphragm is used as the aperture 13, this is not limitative, but a pin hole may be used instead.

What is claimed is:

1. In an optical inspection apparatus including an illuminating block for illuminating a sample with collimated light, an observing optical system for forming an image of a brightness pattern exhibiting a condition of said sample from transmitted light or reflected light from said sample, and an observing block for observing said image, the improvement wherein said observing optical system comprises:

an object side lens arranged on an object side close to said sample;

an image side lens arranged on an image side remote from said sample;

said object side lens and said image side lens being arranged such that said object side lens and said image side lens have focal points coincident to each other, forming a both-side telecentric optical system for acting on said transmitted light or said reflected light to form said image of the brightness pattern exhibiting the condition of the sample, an aperture stop arranged on said focal points or in the vicinity thereof; and a screen arranged on a back focal point of said image side lens or in the vicinity thereof for having said image of the brightness pattern exhibiting the condition of the sample being projected thereon;

and wherein said observing block is arranged such that said image of the brightness pattern exhibiting the condition of said sample projected on said screen is observed from a back side of said screen remote from said sample.

2. An optical inspection apparatus according to claim 1, wherein said illuminating block includes a half mirror arranged between said object side lens and said image side lens for reflecting said emitted light toward said sample, a plurality of light sources for emitting light toward said half mirror at respective angles of emission different from each other, and a lighting control block for selectively lighting one of said plurality of light sources.

3. An optical inspection apparatus according to claim 2, wherein said light sources are each formed by an LED constructed to emit a divergent pencil of rays.

4. An optical inspection apparatus according to claim 1, wherein at least one of said object side lens and said image side lens is an aspheric lens.

5. An optical inspection apparatus according to claim 2, wherein at least one of said object side lens and said image side lens is an aspheric lens.

6. An optical inspection apparatus according to claim 3, wherein at least one of said object side lens and said image side lens is an aspheric lens.

7. An optical inspection apparatus according to claim 1, including means for rotating said screen when said sample is observed.

8. An optical inspection apparatus according to claim 2, including means for rotating said screen when said sample is observed.

9. An optical inspection apparatus according to claim 3, including means for rotating said screen when said sample ms observed.

10. An optical inspection apparatus according to claim 4, including means for rotating said screen when said sample is observed.

11. An optical inspection apparatus according to claim 1, wherein said observing block includes a camera for picking up said image of said sample projected on said screen.

* * * * *